United States Patent
Hartman et al.

(10) Patent No.: US 10,762,167 B2
(45) Date of Patent: Sep. 1, 2020

(54) DECISION SUPPORT TOOL FOR CHOOSING TREATMENT PLANS

(71) Applicant: Varian Medical Systems International AG, Zug (CH)

(72) Inventors: Joona Hartman, Espoo (FI); María Isabel Cordero Marcos, Espoo (FI); Esa Kuusela, Espoo (FI); Jarkko Yrjana Peltola, Tuusula (FI); Janne Ilmari Nord, Espoo (FI)

(73) Assignee: Varian Medical Systems International AG, Zug (CH)

( * ) Notice: Subject to any disclaimer, the term of this patent is extended or adjusted under 35 U.S.C. 154(b) by 867 days.

(21) Appl. No.: 14/040,479

(22) Filed: Sep. 27, 2013

(65) Prior Publication Data
US 2015/0095044 A1   Apr. 2, 2015

(51) Int. Cl.
*G06Q 50/00* (2012.01)
*G06F 19/00* (2018.01)
(Continued)

(52) U.S. Cl.
CPC ............ *G06F 19/00* (2013.01); *A61N 5/103* (2013.01); *G16H 50/20* (2018.01); *A61N 2005/1041* (2013.01)

(58) Field of Classification Search
CPC ........ G06Q 50/22; G06Q 50/24; G06Q 40/08; G06Q 10/10; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17;
(Continued)

(56) References Cited

U.S. PATENT DOCUMENTS

| 7,796,731 B2 | 9/2010 | Nord |
| 7,801,270 B2 | 9/2010 | Nord |

(Continued)

FOREIGN PATENT DOCUMENTS

CA    2813643 A1    4/2012

OTHER PUBLICATIONS

U.S. Appl. No. 14/040,468 (unpublished), filed Sep. 27, 2013, entitled "Automatic Creation and Selection of Dose Prediction Models for Treatment Plans," 42 pages.
(Continued)

*Primary Examiner* — Tran N Nguyen
(74) *Attorney, Agent, or Firm* — Kilpatrick Townsend & Stockton LLP

(57) ABSTRACT

Patient data can be used to determine input values to different estimation functions for different treatment types. The estimation functions can each be used to estimate one or more outcome values for the respective treatment. A quality score can be determined using the outcome value(s). A first treatment plan having an optimal quality score can be identified, e.g., by displaying the treatment plans with the quality scores, which may correspond to the outcome values.

18 Claims, 8 Drawing Sheets

(51) Int. Cl.
    *A61N 5/10*     (2006.01)
    *G16H 50/20*     (2018.01)
    *G06Q 10/00*     (2012.01)

(58) Field of Classification Search
CPC ........ G16H 20/30; G16H 20/40; G16H 20/60;
G16H 20/70; G16H 20/90; G16H 30/00;
G16H 30/20; G16H 30/40; G16H 40/00;
G16H 40/20; G16H 40/40; G16H 40/60;
G16H 40/63; G16H 40/67; G16H 50/00;
G16H 50/20; G16H 50/30; G16H 50/50;
G16H 50/70; G16H 50/80; G16H 70/00;
G16H 70/20; G16H 70/14; G16H 70/60;
G16H 80/00
See application file for complete search history.

(56) References Cited

U.S. PATENT DOCUMENTS

| | | | |
|---|---|---|---|
| 7,809,107 | B2 | 10/2010 | Nord |
| 7,817,778 | B2 | 10/2010 | Nord |
| 8,009,804 | B2 | 8/2011 | Siljamak |
| 8,085,899 | B2 | 12/2011 | Nord |
| 8,331,532 | B2 | 12/2012 | Nord |
| 2003/0177039 | A1 | 9/2003 | Nicholas et al. |
| 2005/0131738 | A1 | 6/2005 | Morris |
| 2009/0154644 | A1 | 6/2009 | Nord et al. |
| 2009/0240523 | A1 | 9/2009 | Friedlander et al. |
| 2009/0299766 | A1 | 12/2009 | Friedlander et al. |
| 2010/0204920 | A1 | 8/2010 | Dranitsaris et al. |
| 2010/0303205 | A1 | 12/2010 | Kapoor et al. |
| 2011/0082712 | A1 | 4/2011 | Eberhardt et al. |
| 2011/0106749 | A1 | 5/2011 | Krishnan et al. |
| 2012/0016690 | A1* | 1/2012 | Ramarajan ............ G06F 19/345 705/2 |
| 2012/0136194 | A1* | 5/2012 | Zhang .................... A61N 5/103 600/1 |
| 2012/0310615 | A1 | 12/2012 | Moore et al. |
| 2013/0077752 | A1 | 3/2013 | Zankowski |
| 2013/0085343 | A1 | 4/2013 | Toimela et al. |

OTHER PUBLICATIONS

Yuan, Lulin, et al., "Quantitative analysis of the factors which affect the interpatient organ-at-risk dose sparing variation in IMRT plans," Med. Phys., Nov. 2012, vol. 39, No. 11, pp. 6868-6878.

Appenzoller, Lindsey, M., et al., "Predicting dose-volume histograms for organs-at-risk in IMRT planning," Med. Phys., Dec. 2012. vol. 39, No. 12, pp. 7446-7461.

International Search Report and Written Opinion dated Mar. 6, 2015 in PCT/IB2014/064936, 11 pages.

Office Action, dated Nov. 19, 2015, in related U.S. Appl. No. 14/040,468; 29 pages.

Zhu, Xiaofeng, et al., "A planning quality evaluation tool for prostate adaptive IMRT based on machine learning," Med. Phys., Feb. 2011, vol. 38, No. 2, pp. 719-726.

U.S. Appl. No. 14/040,468, Final Office Action dated May 19, 2016, 12 pages.

U.S. Appl. No. 14/040,468, "Non-Final Office Action", dated May 2, 2017, 32 pages.

\* cited by examiner

700

710 — Receive a plurality of sets of outcome values for different treatment plans 720 — Receive, from a user, criteria for identifying an optimal quality score 730 — Identify treatment plans having outcome values satisfying threshold criteria 740 — Assign one or more quality scores to each treatment plan using remaining criteria 750 — Sort treatment plans by a designated quality score

FIG. 7

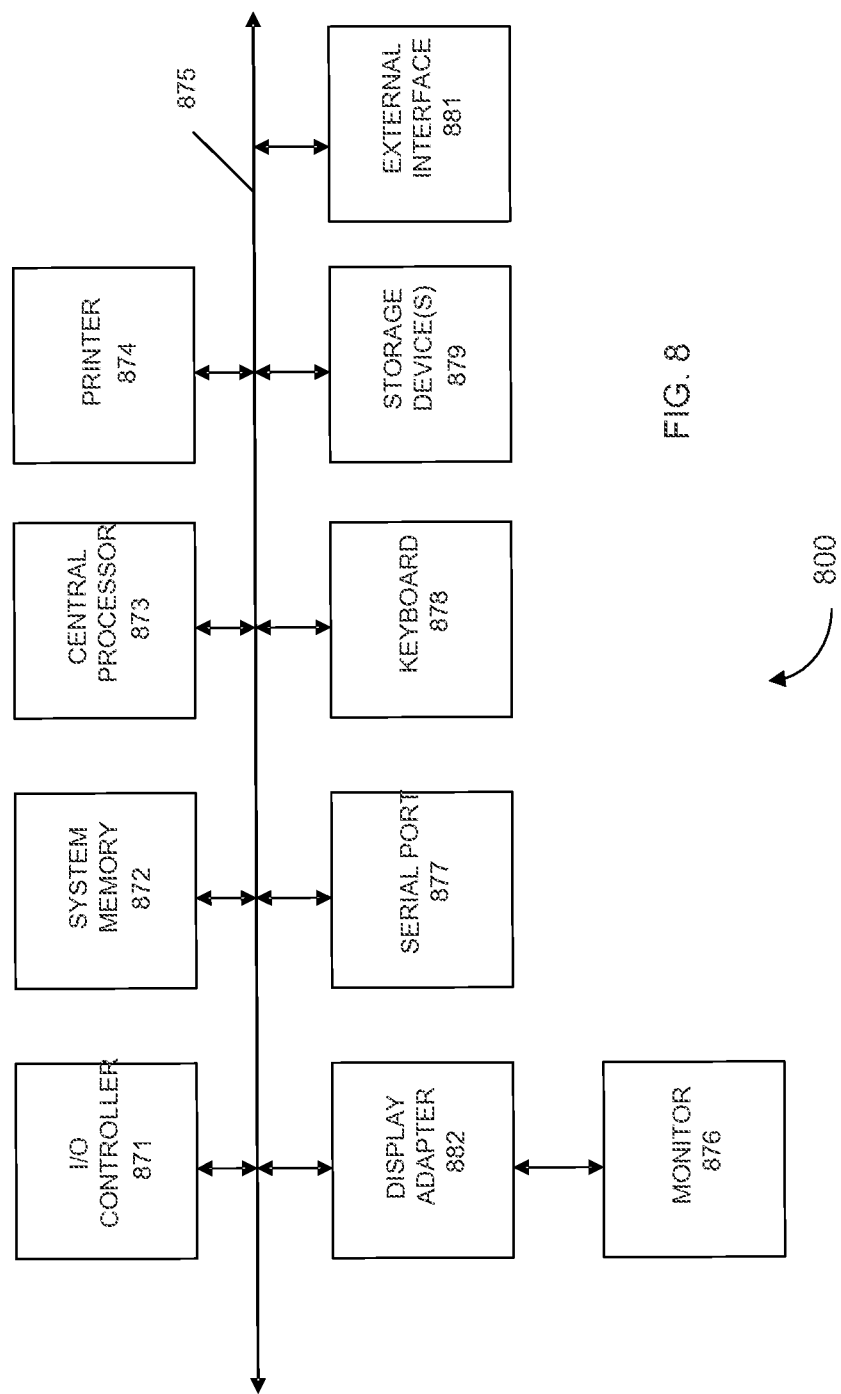

DECISION SUPPORT TOOL FOR CHOOSING TREATMENT PLANS

CROSS-REFERENCES TO RELATED APPLICATIONS

This application is related to commonly owned and concurrently filed U.S. patent application No. 14/040,468, filed Sep. 27, 2013, now U.S. Pat. No. 9,827,445, entitled "Automatic Creation And Selection Of Dose Prediction Models For Treatment Plans", the disclosure of which is incorporated by reference in its entirety.

FIELD

The present disclosure relates generally to treatment planning for treating a tumor, and is more particularly directed for choosing a treatment plan based on estimation models for different treatments.

BACKGROUND

There are multiple techniques for treating a tumor, e.g., radiation treatment, chemotherapy, and surgery, each of which may encompass several techniques. For example, the radiation treatment may be photon or proton. It can be very time-consuming to produce a treatment plan. And, only once a treatment plan has been produced may physician identify that the treatment plan is not suitable.

Currently, the physician will choose a treatment plan based on prior experience, e.g., radiation treatment using photons. The photon treatment plan is then generated. Once the photon treatment plan has been generated, the position analyzes the treatment plan to determine whether the treatment plan satisfies certain criteria (e.g., whether it falls below certain criteria). At that point, the physician has to generate a treatment plan for different treatment, e.g., using protons instead. At that point, the physician may choose between the two treatment plans, or possibly generate more treatment plans for other treatments.

As an example for radiation treatments, a physician can provide some kind of prescription and requirements for the plan, e.g., must save the parotid gland or spine, and the target or the cancerous tissue requires at least sixty grays (unit of radiation). A dosimetrist or physicist then spends several hours to create the treatment plan for a patient, where the treatment plan is for the selected treatment type. The dosimetrist or physicist tries to achieve a good plan by using optimization algorithms, manually placing fields from which direction to have the radiation travel, and setting some blocks to prevent radiation from hitting critical organs from certain directions. Only after all this work does the position review the treatment plan, possibly finding that the dose distribution of the radiation treatment plan doesn't fill all (or critical ones) of the requirements that the physicians has specified. The physician may decide that the treatment plan a sufficient, that the treatment plan for the previously selected treatment type needs to be refined further, or a new treatment plan for different treatment type should be generated.

A physician may be able to determine whether the optimized treatment plan is roughly what one would be able to achieve. When the optimized treatment plan is below expectations, further refinement may be chosen. But, such a process does not guide the physicians decision about whether to refine the treatment plan for the current treatment type, or generate a treatment plan for a new treatment type. Only notice that optimize is not acceptable, the physician may decide to try new treatment type at this late stage. For example, a physician may decide to try proton treatment, for example, because the proton facility is available. Again, a dosimetrist would use several hours to generate a new plan. And, the position would later evaluate what was possible to achieve. Thus, it a long process.

Therefore, it is desirable to provide new tools that allow a physician to determine early on what type of treatment plan should be pursued.

BRIEF SUMMARY

System and methods can provide alternative treatment strategies to a user for evaluation. For example, a quality of the treatment plans is estimated and presented to the user for comparison and choosing a clinically best (or otherwise optimal) treatment strategy for the given patient. For example, the physician may notice that photon treatment is not a good alternative for the specific patient because the left parotid can not be spared with photon treatment or that stereotactic radiation treatment is a good alternative for surgery for a patient that is afraid of surgery.

According to one embodiment, patient data is used to determine input values to different estimation functions for different treatment types. The estimation functions are each used to estimate one or more outcome values for the respective treatment. A quality score is be determined using the outcome value(s). A first treatment plan having an optimal quality score is identified, e.g., by displaying the treatment plans with the quality scores, which may correspond to the outcome values.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 7 is a flowchart of method 700 for identifying the treatment plan having an optimal quality score according to embodiments of the present invention FIG. 8 shows a block diagram of an example computer system 800 usable with system and methods according to embodiments of the present invention.

DEFINITIONS

Figure 1:
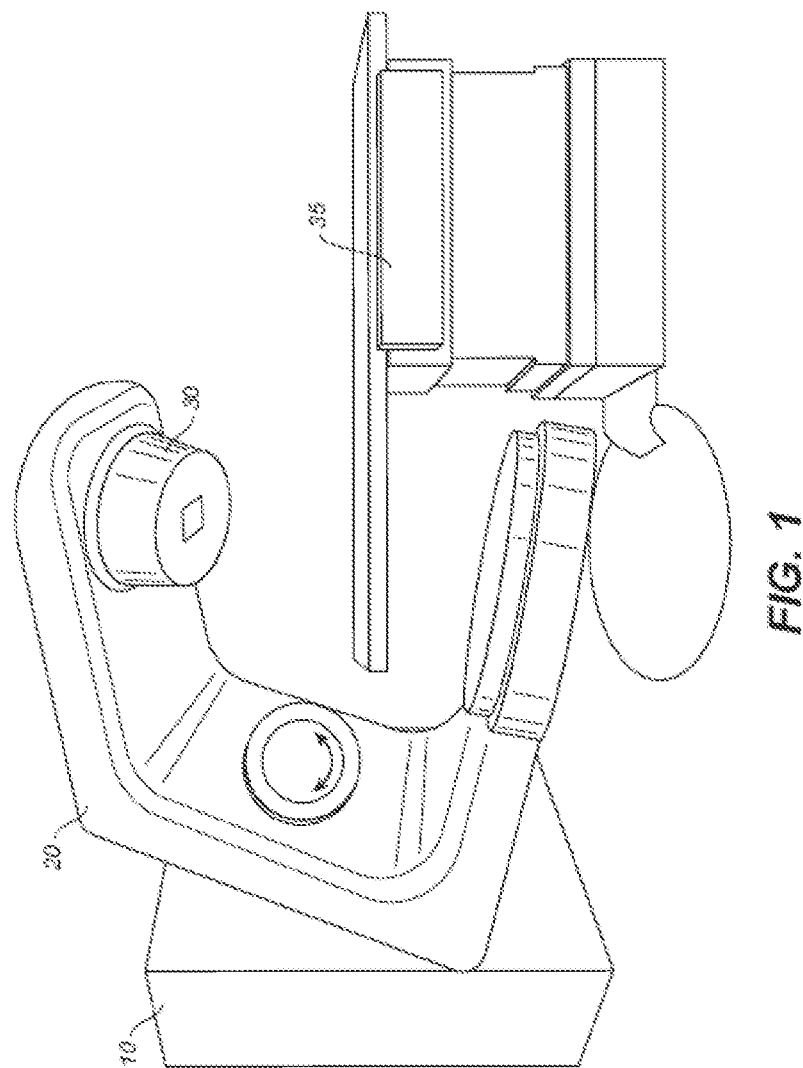
FIG. 1 is a perspective view of a radiation therapy system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types (strategies) of radiation treatments. Other treatment types can include chemotherapy and surgery. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "treatment plan" can include a dose distribution, machine parameters for achieving the dose distribution for a given patient, and information about the given patient. A dose distribution provides information about the variation in the dose of radiation with position. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the horizontal axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

A "dose prediction model" receives patient data and outputs a dose distribution that is predicted to be obtainable. Different types of radiation treatments can have different models. The patient data can include diagnostic information (e.g., general tumor location or stage information) and geometric information (e.g., the spatial geometry of the tumor and of other organs in the patient). A particular model can have an accuracy (reliability) associated with the predicted dose distribution. The accuracy can be determined from a set of test treatment plans whose dose distribution has been determined via other means (e.g., by optimizing a cost function). For example, the accuracy can be determined based on how well the model predicts the actual dose distributions obtained by optimizing a cost function.

An "estimation model" receives input values about the patient and provides outcome values for a particular treatment type. Different treatment types can have different estimation models, where treatment type can correspond to a particular estimation function. These estimation models may be determined from previous treatment plans and the outcomes for the patients. For a particular treatment type, each outcome value can have a corresponding estimation subfunction. The estimation subfunctions can be determined independently, and may operate independently for determining various outcome values of a particular treatment type.

A "outcome value" refers to a value that indicates a predicted quality of the treatment, such as an effect of the treatment on the patient (e.g., organ failure probability) and a property resulting from the treatment (e.g., treatment time). A predicted dose distribution can be used to determine an outcome value, e.g., an effect of the treatment on the patient. A "quality score" can correspond to a particular outcome value were be a function of multiple outcome values. A quality score can provide a measure for comparing one treatment plan to another. An "optimal quality score" can refer to a quality score that satisfies one or more criteria or is better than another quality score. An example of a criterion is that the optimal quality score is any quality score above a threshold. Another example is a quality score that has the highest quality score or in a highest N (e.g., 5) or top X % (e.g., 10%) of the quality scores. A list of treatment plans and corresponding quality scores indicates an optimal quality score, given the correspondence between treatment plans quality scores.

DETAILED DESCRIPTION

Estimation models can be used to select a treatment plan from among various treatment types for a new patient. The estimation models can be determined based on treatment plans that have been implemented for patients and the resulting outcomes. The system can then use the estimation models to predict what is a suitable treatment plan (e.g., best or meeting a criteria) for the patient. A treatment plan can be selected with confidence, and the treatment plan can be generated. Thus, a decision support tool can be provided for choosing a treatment strategy.

As an example, a support tool can have multiple models for different treatment types. For instance, one model (function) can be generated for photon radiation treatment. And, another model can be generated for another type of radiation treatment, e.g., protons for heavy ions. Other treatment strategies can include chemotherapy and surgery. Further treatment strategies can include combinations of different treatment strategies. Each of these treatment strategies can have their own model that estimates outcome values for a treatment plan corresponding to the treatment strategy.

I. Treatments

Embodiments can be used to select among treatment plans for various treatment types (strategies). Search even attempts maybe organized into a particular class, e.g., radiation treatments, which has several treatment types within the class. Some examples of treatment types are described below.

A. Radiation Systems

Figure 2:
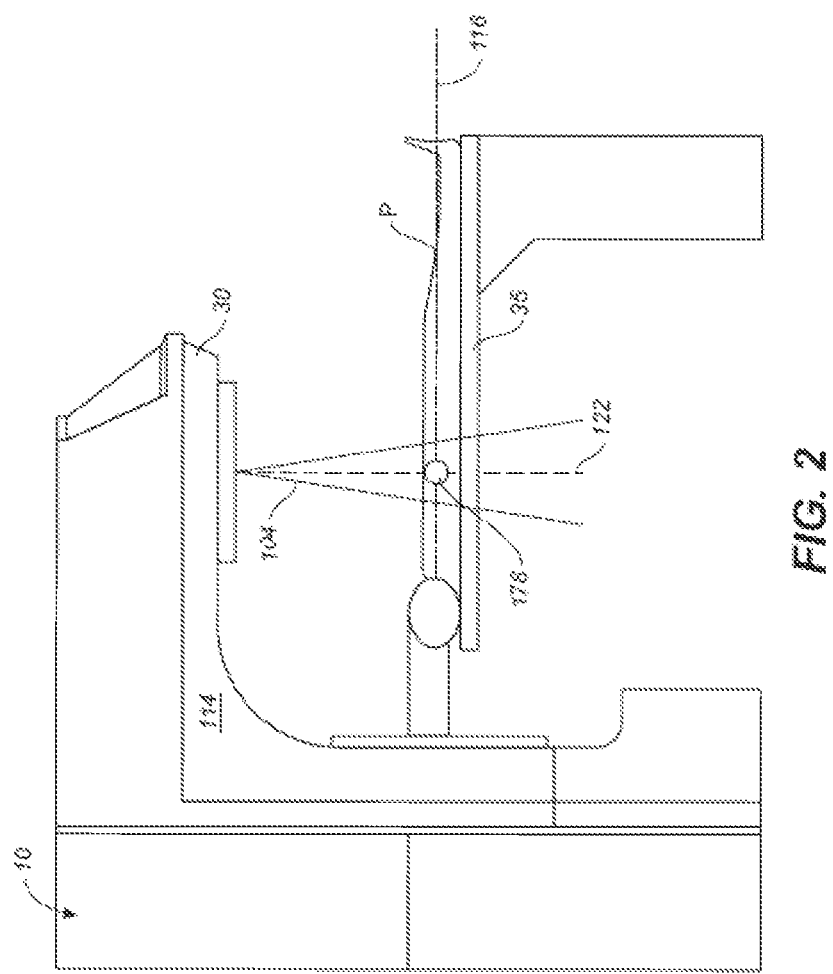
FIG. 2 is a side view of a radiation therapy system.

FIGS. 1 and 2 depict a radiation therapy system of the type which may be used in connection with the present invention. Referring to FIG. 1, a perspective view of radiation therapy system (in this case a linear accelerator) is shown. Typically, such a system is capable of generating either an electron (particle) beam or an x-ray (photon) beam for use in the radiotherapy treatment of patients on a treatment table 35. Other radiation therapy systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) which includes operational electronics for controlling the different modes of operation of the accelerator. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation therapy system of the type which may be used in connection with the present invention is shown. A patient P is shown lying on treatment table 35. X-rays formed as described above are emitted from the target in treatment head 30 in a divergent beam 104. Typically, a patient plane 116, which is perpendicular to the page in FIG. 1B, is positioned about one meter from the x-ray source or target, and the axis of gantry 20 is located on plane 116, such that the distance between the target and isocenter 178 remains constant when gantry 20 is rotated. Isocenter 178 is at the intersection between patient plane 116 and the central axis of beam 122. A treatment volume to be irradiated is located about the isocenter.

"Jaws" (not shown) or x-ray collimators comprising an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 1B) is positioned at the exit of head 30, to further shape the x-ray beam. Since its introduction in 1990 the MLC has become a standard feature of most radiation therapy systems. Current MLCs sold by the assignee of the present invention use up to 120 individually controllable leaves, typically thin slices of tungsten, that can be moved into or out of the x-ray beam under the control of system software. The MLC can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to the isocenter in the path of the x-ray beam, is defined by the jaws, the angle of the head and the MLC. In IMRT the leaves of the MLC are moved, such that the treatment volume comprises the total volume exposed during the course of a treatment. In arc therapy, the gantry is moved while radiation is delivered.

Modern radiation therapy techniques involve the use of a treatment plan designed to irradiate a desired target volume, usually corresponding to a tumor, with a desired dose of x-rays (or other radiation). Most treatment planning involves the use of the MLC to provide conformal and/or intensity modulated irradiation. Generally speaking, a treatment plan comprises irradiating one or more selected portions of the treatment volume with a calculated dose of x-rays, and often involves irradiating a treatment area from a plurality of different angles which, in the case of arc therapy, may be delivered while the gantry is rotated. Various treatment planning software and other tools are available for developing specific treatment plans, and the details of the various techniques for creating such plans are known and will be described in further detail below. Again, generally speaking, after a treatment plan is created it is implemented, in part, by controlling the angle of incidence and the leaves of the MLC so as allow the desired radiation dose to reach the selected portions of the treatment volume from the selected angles or while the gantry is rotating. In the simplest type of treatment plan, the MLC is adjusted to provide static conformal irradiation of a specific site from a single angle. In more complex plans, the leaves are moved into different positions between or during irradiations. The leaves of the MLC can either be moved iteratively into different positions while the beam is off, with irradiation between movements, (such that the leaves are static during x-ray emission), or they can be continually moved during irradiation in a "sliding window" or other variable aperture technique. As noted above, an important aspect of the conformal and IMRT techniques that are associated with the use of MLCs is the ability to both provide a desired dose of radiation to a target volume while minimizing the dose delivered to adjacent healthy tissue.

As described in more detail in the Background section above, several techniques have been developed to create treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a treatment plan. Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk that can only receive a much lower, maximum prescribed amount of radiation without risk of damage. This volumetric information along with the prescribed dose limits and similar objectives set by the medical professionals is the basis for calculating an optimized dose distribution and the treatment plan to deliver it. The volumetric information may, for example, be reduced to an objective function or a single FIGURE of merit that accounts for the relative importance of various trade-offs inherent in such a plan, along with constraints that must be met for the plan to be medically acceptable or physically possible.

Treatment planning algorithms can account for the capabilities of the specific radiation therapy system they are used with. For example, the type, energy level and fluence of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

B. Other Treatments

As described above, there are several different radiation treatment types, such as photon, proton, and heavy ion, corresponding to different particle types. Radiation treatment type can also depend on how the radiation is provided, e.g., as external beam radiation or as an internal radiation (brachytherapy). Other types of treatment include chemotherapy and surgery.

As an example for chemotherapy, there may be multiple (e.g., tens of) drugs available that have different effectiveness depending on multiple known and unknown properties (such as, type and stage of the cancer, genomic profile of the cancerous cells), as well as cause different types of adverse effects on the patient. In order to maximize the therapeutic effect of chemotherapy, a most effective drug can be chosen together with an effective dosage (e.g., amount of drug given and treatment schedule).

As an example for surgery, surgery treatments can be characterized by the amount of tissue that is removed during the surgery, including what tissue is to be removed, e.g., only the primary tumor, part of the primary tumor, primary tumor and nodes, primary tumor and part of the surrounding healthy tissue (such as, whole breast removal (mastectomy), partial breast removal (lumpectomy), removal of part of the lung, removal of entire lung (pneumonectomy)). The amount of tissue can then affect the outcome values, such as side effects, pain experience, expected lifetime, etc. The size and location of the tumor can affect what type of surgery is possible. Patient's health indicators may restrict the type of surgery that can be applied and affect the probability of complications and recovery time.

A treatment plan can also include a plurality of treatment types. For example, combination therapies can be used where any combination of radiotherapy, chemotherapy, and surgery are used. For example applying a regime of chemotherapy prior or during radiotherapy can make the therapeutic response better and a lower radiation dose can be used. Thus, an estimation function can be determined for a particular set of treatment types. Different treatment plans can also be developed for a different order of applying the different treatment types.

II. Selecting Treatment Plan Based on Estimation

Embodiments can be used in advance in the prescription phase by the physician to decide between treatment plans for different strategies. For example, outcome values can be provided as a summary of the estimated treatment. Outcome values for different treatment plans can be compared to select one with the best estimated outcome values.

Figure 3:
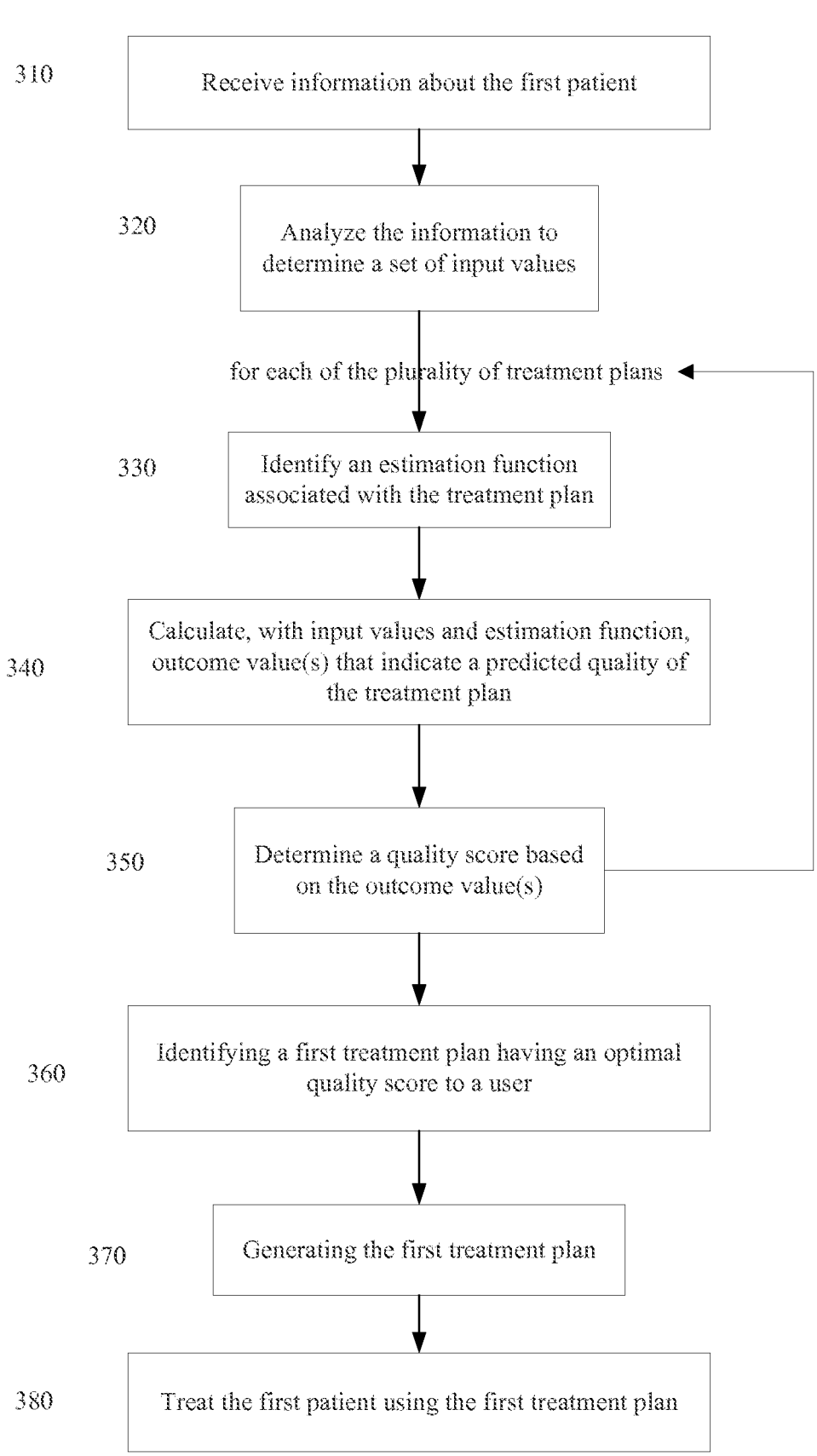
FIG. 3 is a flowchart of method 300 of selecting among a plurality of treatment plans for treating a tumor of a first patient according to embodiments of the present invention.

FIG. 3 is a flowchart of method 300 of selecting among a plurality of treatment plans for treating a tumor of a first patient according to embodiments of the present invention. Method 300 may be implemented entirely or partially using a computer system, as can other methods described herein. The plurality of treatment plans can be of various treatment types, as described herein.

In step 310, information is received about the first patient. The patient information can include diagnostic information (e.g., general tumor location or stage information) and geometric information (e.g., the spatial geometry of the tumor and of other organs in the patient). The patient data can be received through various channels, e.g., patient images, questionnaires, and historical information about the patient. Further details about patient information is described below.

In step 320, the information is analyzed to determine a set of input values. The patient information can be analyzed to identify specific quantitative values that correlate to various outcomes. The received information can include an input value, or an input value can be derived from the received information. The analysis can be statistical in nature. For example, a patient image can be analyzed to determine an average width, height, or length of the tumor or other organs.

In step 330, an estimation function associated with the treatment plan is identified for each of the plurality of treatment plans. The estimation function can be generated based on outcomes of other patients using the treatment plan. Examples outcomes include expected lifetime, 5 year survival rate, remission rate or disease free survival; organ specific failure probability (e.g., of parotid glands) and other side effects; and quality of life indicator reported by the patient (e.g., subjective pain level experience and recovery time).

At least two of the plurality of treatment plans are for different types of treatments. For example, one treatment plan can be for photon radiation and another treatment plan for chemotherapy or surgery. In one embodiment, there can be more than one treatment plan for each treatment type. In various implementations, one estimation function can be identified for each treatment type (e.g., using the input values to select the estimation function corresponding to a particular treatment plan for a particular treatment type) or multiple estimation functions can be identified for treatment type.

In step 340, the set of input values and the identified estimation function are used to calculate one or more outcome values that indicate a predicted quality of the treatment plan for each of the plurality of treatment plan. The set of input values can be input into the estimation function, which can output the one or more outcome values. The estimation function can be of various forms. For example, an estimation function can be multidimensional function that defines a surface for an outcome value. In one embodiment, each outcome value is determined using a different estimation subfunction, where the subfunctions can be calculated independently (e.g., each subfunction can be a different multidimensional function that defines a surface for the corresponding outcome value). Other functional forms include neural networks, Bayesian networks, hierarchical clustering, and decision trees.

In step 350, a quality score is determined based on the one or more outcome values for each treatment plan. In one embodiment, the quality score can be one of the outcome values, or simply the outcome value when there is only one outcome value. In another embodiment, the quality score can be determined from a quality score function that uses specific criteria to determine the quality score from the outcome values. For example, the outcome values can be analyzed to identify treatment plans that satisfy one or more first criteria (e.g., a particular outcome value can be required to be above a threshold). In addition (e.g., remaining treatment plans satisfying the first criteria) or separately, a formula can be used for the outcome values (e.g., a weighted sum) to obtain a quality score. A physician or scientist can provide any such criteria or formulas.

In step 360, a first treatment plan having an optimal quality score is identified to a user. The first treatment plan can be identified in various ways. For example, a list of treatment plans and corresponding quality scores can be provided, wherein the identification is by identifying the first treatment plan with its corresponding quality score having a score higher than other plans in the list. Alternatively, the first treatment plan can be highlighted (e.g., only providing the first treatment plan, using bold, or other coloring), such that the corresponding quality score does not need to be provided. The identification of the first treatment plan can be in response to request from a user, where the request can specify criteria for identifying the first treatment plan. For instance, the user can specify that he/she is looking for a treatment plan having the highest value for particular outcome value. Further, the optimal quality score can correspond to any quality score satisfying a particular criteria, and thus does not have to be a quality score that has the best value.

In step 370, the first treatment plan is generated. For example, in response to the identification of the first treatment plan as likely being a good treatment plan, the user (e.g., a doctor) can generate the first treatment plan. In one aspect, only after the first treatment plan is identified is the first treatment plan generated. In this manner, the expensive cost of generating the first treatment plan is not incurred until it is known that the first treatment plan is a good candidate. Thus, resources are saved.

The generation of the first treatment plan can involve further computation, e.g., using optimization techniques to determine optimal settings for the treatment plan. An example technique for optimization for radiation therapy is described in U.S. Pat. No. 7,801,270, which is incorporated by reference. The input values and the outcome values can be used in a generation of the treatment plan. Further, intermediate values determined from the input values can also be used, such as a predicted dose distribution.

In step 380, the first treatment plan is used to treat the first patient. The first patient can undergo treatment for an amount of time specified by the generated first treatment plan. Outcomes for the first patient can be tracked, and these outcomes can be used to revise the corresponding estimation function.

The estimation function can help determine outcome values that are likely achievable, if a treatment plan was actually developed. For example, whether it is likely that a nearby healthy organ can be saved may be determined. The general side effects may also be identified, and then used by a physician or the system to determine a suitable plan. One might be able to eventually tailor a non-selected treatment to maybe be a little bit better, but the estimation functions can give a rough idea of which one is generally better.

III. System

Figure 4:
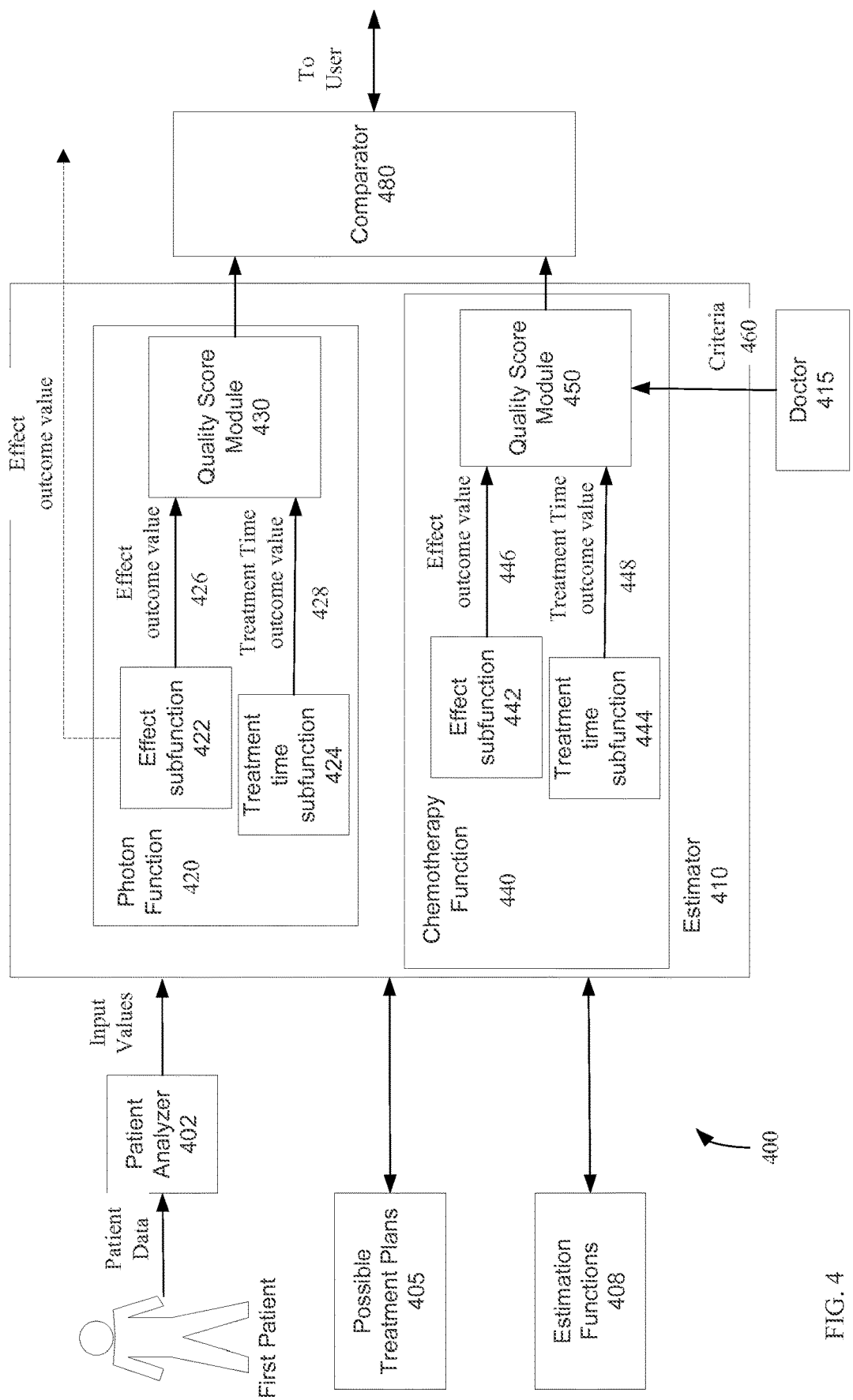
FIG. 4 shows a system 400 for estimating quality scores of treatment plans according to embodiments of the present invention.

FIG. 4 shows a system 400 for estimating quality scores of treatment plans according to embodiments of the present invention. All or parts of system 400 may be comprised in a single computer or multiple computers. Note that system 400 would not include the patient.

A patient analyzer 402 can receive patient data about the first patient. The patient data can be obtained from a variety of sources, e.g., images taken of the first patient, user input provided by the first patient, databases storing patient data, and information about other tests performed on the first patient. Patient analyzer forward to receive the patient data directly from machines that took images or can be loaded by other means. Patient analyzer 402 can analyze the patient data to obtain input values, to be used in the estimation models. Patient analyzer 403 can sift through the patient data according to prescribed rules to identify specific information and can perform computations on the data (e.g., images) to obtain physical properties of the patient (e.g., tumor size and relative location two other organs).

Estimator 410 can use the input values to estimate outcome values for different treatment plans 405. Information about possible treatment plans 405 can be stored (e.g., and local memory, hard drive, or external database) for retrieval by estimator 410. Estimator 410 can retrieve estimation functions (models) they correspond to the possible treatment plans 405. In one embodiment, a doctor 415 can select the treatment plans for which an estimation is computed.

Estimator 410 is shown as using two estimation functions: one for photon radiation treatment and one for chemotherapy treatment. Although only two estimation functions are shown, estimates for additional treatments may be computed. Photon function 420 provides two outcome values: an effect outcome value 426 and treatment time outcome value 428. Examples of effect outcome values are described in more detail below. To provide these two outcome values, different estimation subfunctions are shown. Effect subfunction 422 receives input values and provides the effect outcome value. Treatment time subfunction 424 receives input values and provides the treatment time or become value. A quality score module 430 uses these outcome values to determine a quality score for the photon treatment.

Similarly, chemotherapy function 440 provides the same two outcome values: an effect outcome value and treatment time outcome value. These two outcome values for chemotherapy function 440 would likely differ from the two outcome values for photon function 420. Effect subfunction 442 provides the effect outcome value 446, and treatment time subfunction 444 provides treatment time outcome value 448. A quality score module 450 uses these outcome values to determine a quality score for the chemotherapy treatment.

As shown, effect subfunction 422 can output an outcome value directly, and not just provide the value to module 430. Other subfunctions can certainly provide a corresponding outcome value. In one embodiment, a particular outcome value can be used directly as a quality score for the corresponding treatment plan.

Doctor 415 can provide criteria 460 for determining the quality scores for the various estimation functions. Criteria 460 can include various information, such as desired treatment and/or hospitalization time, time of availability of machines and/or personnel, and other criteria. Each criterion can input potentially as a strict cutoff that must be satisfied, as a criteria for sorting, or as a weighting for a particular outcome. As an example, it might be that proton treatment would be available after one week, or the photons treatment is available immediately. As another example, one treatment may be more expensive, or take a longer time to plan. The criteria can be used make decisions (e.g., determine quality score) for identifying a treatment plan based on the different criteria. Thus, system 400 can rate between having this photon treatment now or the proton treatment a week later. The advantages and disadvantages of each treatment plan can be weighted based on estimated outcome.

Comparator 480 can compare the quality scores from the two estimation functions and provide an output to a user. In one embodiment, the comparison is performed in response to request from the user, which may be doctor 415. The request can include criteria 460. Such a request may be performed when outcome values from a subfunctions are provided to comparator 480. For example, comparator 480 can identify outcome values that satisfy particular criteria, and then sort the treatment plans based on other criteria. Comparator 480 can also simply provide a list of treatment plans with corresponding outcome values/quality scores, thereby providing an identification of an optimal quality score.

In another embodiment, comparator 480 can receive one quality score from each of the modules 430 and 450 and perform a comparison based on prescribed rules, e.g., identifying the largest quality score. In various embodiments, the prescribed rules can be provided entirely or partially via criteria 460. A structure for the rules may be set (or one structure selected), where the structure provides the logic operation, but not the specific cutoff values or other criteria.

IV. Values

Various information described herein includes the patient data, input values to an estimation model, and outcome values, as well as criteria for identifying an optimal treatment plan using a quality score. Below are some examples of such information.

Examples of patient data include a size of a patient (e.g., mass or height) and tumor size, as well as patient images and a desired dose. For example, treatment planning can start with (1) images of the treatment volume (e.g., slices from CT or MRI scans) and, (2) the desired dose of radiation which is to be delivered to a target, such as a tumor, within the treatment volume. The patient data or criteria provided by a doctor can also include the maximum dose which can be safely absorbed by tissue structures, such as organs, within the treatment volume that are adjacent to or near the tumor or other target volume. Other examples of patient data includes genetic markers/features, geometric information of structures (such as the tumor or other tissue), age of the patient, body mass index (BMI), contra indicators of the patient, previous treatments, and general medical history details.

As described above, the patient data can be analyzed to determine input values for estimations functions. Some or all of the patient data can be used directly as input values, i.e., no formula or analysis is needed. Other input values are determine from a formula or analysis of the data. For example, particular geometric values can be determined by analyzing the patient images, e.g., by measuring relative distances of objects in the image. As another example, a formula may be used to combine patient data to determine an input value, e.g., a sum of previous treatments or a percentage of genetic markers making the patient at risk. One particular input value is a predicted dose distribution, which can be determined using a prediction model based on the patient data.

Examples of outcome values include values about an effect of treatment and a property of the treatment. An effect of a treatment can relate to a measured or statistically observed biological effect or outcome relating to the patient. Examples include expected lifetime or disease free survival; organ specific failure probability (e.g., of nearby organs, such as parotid glands) and other side effects; and quality of life indicator reported by the patient (e.g., subjective pain level experience). The property of treatment can relate to aspects of the actual treatment plan itself, such as treatment time, hospitalization time, recovery time, a resource indicator (e.g., machine usage or need for experts), and cost.

V. Estimation Functions

As described above, estimation functions can be created for different treatment plans, including different types of treatments. The estimation function may be trained (determined) based on a set of plans that have been previously generated for other patients. The estimation functions can be used as part of a model to determine an optimal treatment plan for a particular patient.

A. Creating

Figure 5:
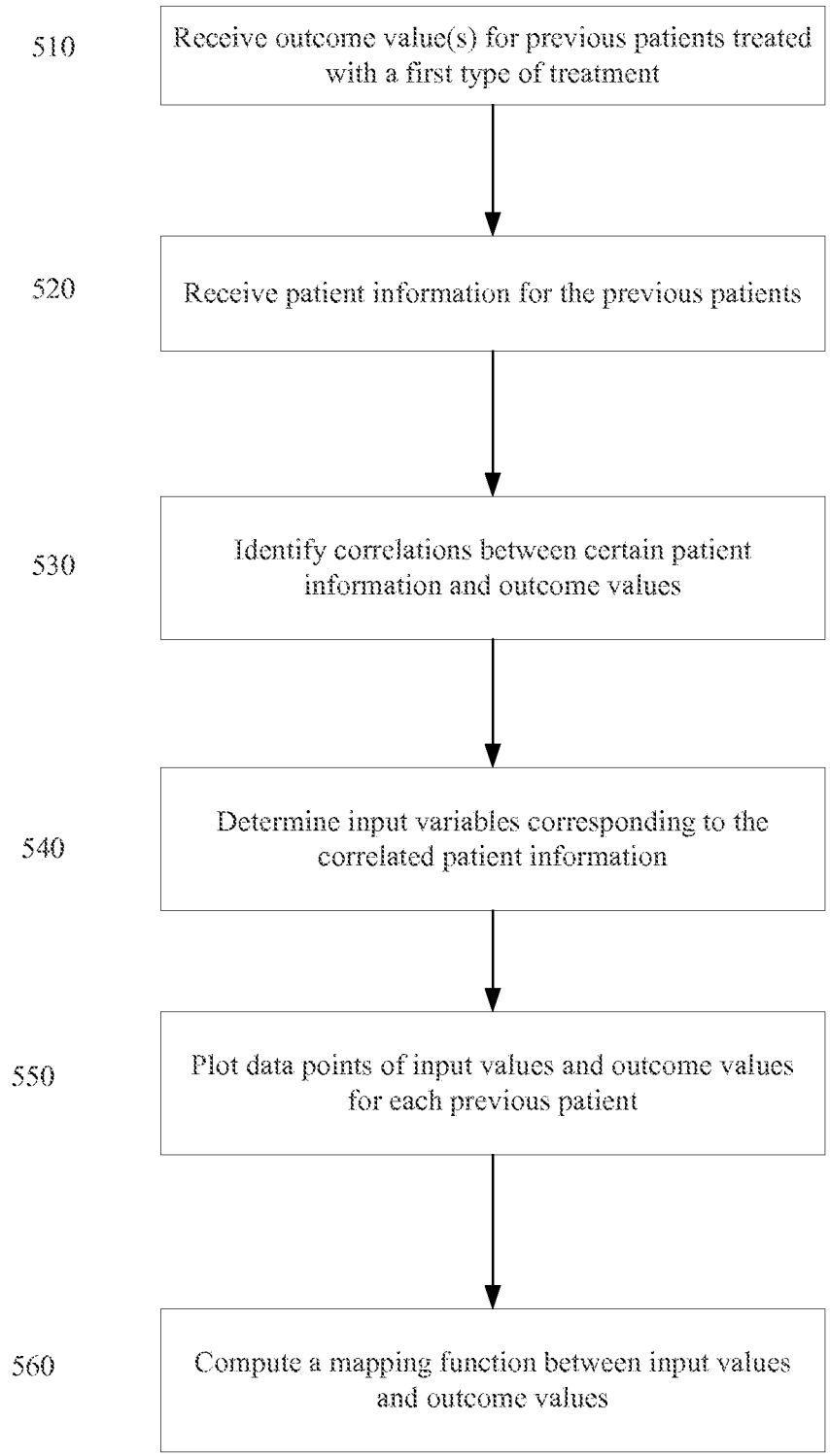
FIG. 5 is a flowchart of a method 500 for creating a estimation function according to embodiments of the present invention.

FIG. 5 is a flowchart of a method 500 for creating a estimation function according to embodiments of the present invention. Method 500 may be used to determine a particular estimation subfunction that outputs a single outcome value, or be used to determine a more general estimation function that provides multiple outcome values for a particular treatment type. Method 500 can be performed by a client computer (e.g., with which a user directly interacts) or a server computer (e.g., that is in communication with a client computer), or a combination of both.

In step 510, outcome value(s) are received for previous patients treated with a first type of treatment. The outcome values can be any outcome of the treatment, such as values described herein. The outcome values may be received directly, or maybe received this general outcome information, which is then analyzed to determine specific outcome values. The previous patients may be treated with different treatment plans, but the treatment type (e.g., proton radiation) is the same for the previous patients.

In step 520, patient information is received for the previous patients. The patient information may be of the same type as is described above. For example, the patient information may include patient images, general physical characteristics, such as age and weight, and medical history. Such patient information can be gathered from databases maintained by medical institutions. Thus, an estimation function can be based on real measurements/statistics (recorded from earlier patient cases) for a specific protocol.

In step 530, correlations between certain patient information and outcome values are identified. The correlations can be determined, for example, using a statistical analysis. For example, they can be determined whether different patient information results in different outcome values, and whether such changes are statistically significant. For instance, an increase in age can be correlated with the statistically significant decline in certain outcomes. Different outcome values can be correlated with different patient information.

In step 540, input variables corresponding to the correlated patient information are determined. The input variables may simply be the specific patient information, such as age or body mass index (BMI). In other embodiments, an input variable can be a combination of different patient data. In one implementation, input variables showing the highest correlation can be chosen for creating the estimation function. In this manner, a better estimation can be obtained by identifying input variables that have the most impact on the outcome values.

In step 550, data points of input values and outcome values are plotted for each previous patient. The data plotting can be performed internally by the computer as part of a clustering or fitting process. Each input variable can be considered a different dimension, with different input values corresponding to different points along that dimension. The plotting can be any mechanism that defines a relative distance among input values. For some input variables, a relative distance between any two different input values can be considered to be the same (e.g., a distance between any two of three different values can be considered to have the same distance).

In step 560, a mapping function between input values and outcome values is computed. Each outcome value can have a different mapping function, which corresponds to a different estimation subfunction. A mapping function provides an outcome value given a specific set of input values. The mapping function can be a multidimensional surface plot. The input values can be mapped to output values, for example, by using clustering, correlation, and functional fitting methods. In one embodiment, the computation of the mapping function is performed by a server.

As an example, a specified functional form (e.g., polynomials) having variable coefficients can be fit to the input values, so as to provide a particular outcome value for any input value. Functional forms such as polynomials, exponentials, or periodic functions can be used. The fitting process can use a least squares minimization process, or other suitable techniques. Such fitting processes can be useful when the input variables and outcomes are continuous in value, or at least have many possible values.

As another example, clustering can be used to identify that certain input values correspond to a same outcome value. Such clustering techniques can be useful when the outcome value are discrete values, which may not have a well-defined distance among the discrete values. Functional forms such as neural networks can be useful for such clustering.

Method 500 can be repeated for different treatment types, and can be repeated for different classes of treatment plans within different treatment types. Once an estimation function has been created, it may be used to estimate outcome value for new patient based on new input values for the new patient.

B. Use Prediction Model as Intermediate within Estimation Model

In some embodiments, a dose prediction model can be used as an intermediate function, e.g., by patient analyzer 402 to determine input values (e.g., dose input values). For example, the radiation dose can be predicted, and, from this radiation dose, then the system can estimate what kind of side effects are likely with the treatment plan. In one embodiment, a dose prediction model can predict the dose value histogram (DVH) for a photon treatment, proton treatment, or heavy ion treatment. Corresponding prediction models can be used for other treatments, e.g., chemotherapy can determine a dose from a drug in the body.

Figure 6:
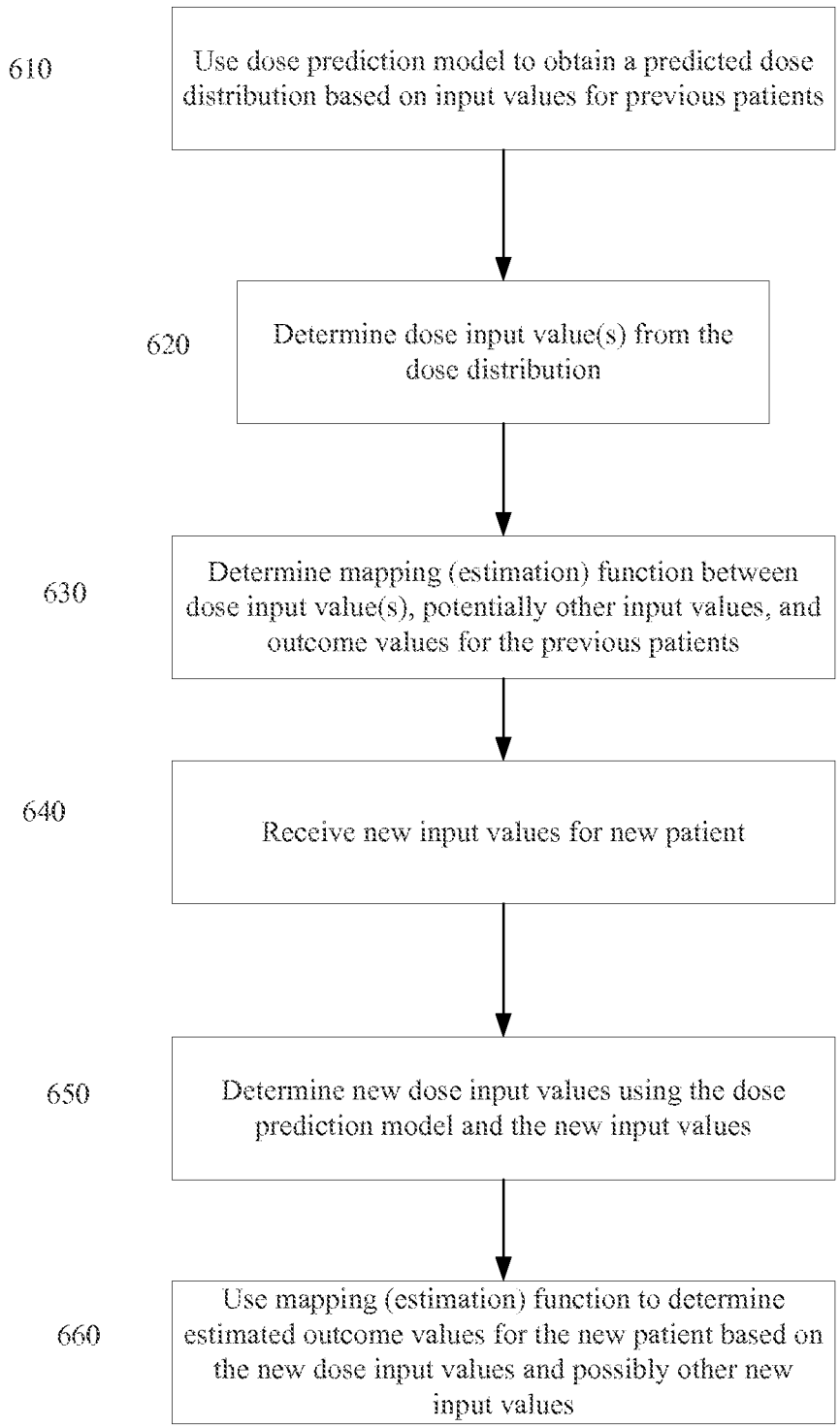
FIG. 6 is a flowchart of method 600 for using a dose prediction model in creating an estimation function according to embodiments of the present invention.

FIG. 6 is a flowchart of method 600 for using a dose prediction model in creating an estimation function according to embodiments of the present invention. Method 600 may be used in conjunction with other methods described herein, as is also the case for combining other methods. In one embodiment, method 600 can be performed by patient analyzer 402.

In step 610, a dose prediction model is used to obtain a predicted dose distribution based on input values for previous patients. The dose prediction model can be determined and used as described in concurrently filed U.S. patent application entitled "Automatic Creation And Selection Of Dose Prediction Models For Treatment Plans." The patient input values can be the same or different as the input values used to directly determine the estimation function.

In step 620, dose input value(s) are determined from the dose distribution. Examples of dose input values are statistical values obtained from the dose distribution. Any term (e.g., statistical terms) determined from a dose distribution can be used. For example, first order terms such as maximum dose, mean dose, median dose, minimum dose, dose in a specific volume percent, and volume percent of a specific dose may be used. Second or higher order terms of the first order terms (e.g., standard deviation, skewness, and kurtosis) are other examples. Other examples include projections of DVHs over principal components (i.e. principal components scores).

In step 630, a mapping (estimation) function between dose input value(s) and potentially other input values to outcome values for the previous patients is determined. The mapping function may be determined as described for method 500, except that now dose input value(s) are used, in addition or by themselves. The other input values may be the same or different than input values used in step 610.

A predicted dose distribution can help in estimating outcome values. For example, there is clinical data and recommendations about accepted dose levels. The data can be based on knowledge that organs have high failure risk after a specific dose level to specific fraction of volume. Further, the system could collect data as what kind of side effects have been observed when these kind of treatments have been applied, which may include a statistical analysis of how likely certain outcomes are. Thus, dose distribution can be used to determine expected outcome and organ failure probabilities. However, estimation models can be determined without a predicted dose distribution.

In step 640, new input values for a new patient are received. The new input values can correspond to the same categories of input values used in step 610. The new input values can be determined from date about the new patient.

In step 650, new dose input value(s) are determined using the dose prediction model and the new input values. The dose prediction model can be used in a similar way as in step 610 to determine a predicted dose distribution for the new patient, which can be used to determine the new dose input values. The new dose input values can be derived in a similar way as in step 620. For example, a statistical value of the predicted dose distribution of the new patient can be computed in a same way as a statistical value in step 620 (e.g., both are an average computed using a same formula).

In step 660, the mapping (estimation) function is used to determine estimated outcome value(s) for the new patient based on the new dose input value(s) and possibly the new input values. In some embodiments, potentially only the new dose input value(s) are used as inputs to the estimation function. If other input values are used, the same or different input values as was used to determine the dose input values may be used. Thus, for the new patient, a system can generate an estimated outcome value. For example, an outcome value could be an indication that there is a 30% chance of a parotid gland not functioning well after treatment.

More than one dose prediction model may be used for different organs. For example, a dose histogram of the dose levels can be predicted for the spine, parotid, and target, and even other organs such lung and other critical organs. These predicted models can be operated independently to obtain different dose input values that are used by a same estimation function.

Other features of the treatment, like fractionation, chemotherapy and surgery also affect complication probabilities. These other treatments can have intermediate functions as well. For example, a predicted dosage of a given drug can be predicted. This dosage can be used as a dose input value to an estimation function to determine to estimate tumor control (shrinkage, or other physical response) and/or side-effect probability, as a function of the predicted dosage for the given drug. The quality score could be a particular calculation of prognosis, which uses these outcome values, which can be done for any of the treatment types. For surgery, a prediction model can predict the amount of tissue to be removed, which can be used as a does input values to estimate a probability of side-effects, e.g., based on the patient's health indicators and other input data.

VI. Use of Outcome Values and Quality Score

As described above, separate estimation functions can be used for different treatment plans to obtain quality scores for the different treatment plans. In one embodiment, the physician can decide based on the quality score which one is the best or suitable model based on the estimate. How the physician decides can be accomplished in various ways, and may include providing criteria to the system (e.g., as a request after outcome values have been determined or as input). For example, the physician may view various outcome values to make the determination. In other embodiments, the system can use criteria to output a specific treatment plan. Regardless, the system can indicate a treatment having an optimal score via the outcome values, e.g., by outputting the outcome values or by combining outcome values via a formula to provide a combined quality score.

One embodiment of comparing quality scores is to produce a report of expected outcome values and then evaluate it by human expert. Different treatments can be ordered by selecting one of multiple ordering filters, for example, order by expected lifetime and exclude treatments with hospitalization time >1 week. Another example is to order by tumor control probability and ignore parotid gland effect (e.g., for a patient with already damaged parotid glands). The outcome values (or more complicated quality scores) of treatment plans satisfying the criteria can be presented, e.g., for a doctor to make a decision to go forward with the one type of plan. In such an instance, the system still identifies an optimal plan, e.g., via the sorting. For instance, logic can account for treatment time, e.g., how long would one fraction take, how long would the whole treatment take, and then the physician could decide based on these factors.

As an example, a patient can have head and neck cancer, and then the system can generate an estimate for proton treatment and photon treatment (potentially different kinds of photon treatment). The estimate for the photon treatment might indicate that it is possible to save the left parotid (salivary gland) but not possible to save the right parotid. And, the estimate for proton treatment might indicate that it is possible to save both parotids with this treatment plan (the indication could be via words, percentages, etc.). In this manner, the optimal treatment plan can be indicated via the estimated outcome value for saving the parotid.

In another embodiment, the system could specifically propose a treatment plan. The system can provide an automatic evaluation (e.g., using criteria provided by a user or set as a default via software) that proposes a plan, along with reasoning (e.g., able to save both parotid glands) for why the treatment plan was identified. If for some patients it is worst to have a long treatment time, then a criteria can be that the treatment time is less than a specified amount or simply sort based on estimated treatment time. For example, if it's a lung cancer patient, it may be difficult for them to stay still for the period of a treatment, and it may be very important for the treatment time to be short. Other patients may be able to take long treatment times, and thus the criteria can change. Thus, the system could weight benefits based on criteria provided by the doctor.

FIG. 7 is a flowchart of method 700 for identifying the treatment plan having an optimal quality score according to embodiments of the present invention. Method 700 can use criteria from a user to identify a treatment with an optimal quality score.

In step 710, a plurality of sets of outcome values are received for different treatment plans. Each set of outcome values can be determined from a different estimation function. And, each of the outcome values within a set can be determined using a different estimation subfunction. The different treatment plans may be each for a different type of treatment.

In step 720, criteria for identifying an optimal quality score is received from a user. The criteria can be received at any time. For example, the criteria may be received after displaying the sets of outcome values to a user. In another embodiment, the user can specify the outcome values for use by a quality score function (e.g., modules 430 and 450) prior to displaying any data to a user. The criteria can be specified in various ways. For example, the criteria may include a formula and/or specific thresholds that are required for certain outcome values.

In step 730, treatment plans having outcome values satisfying threshold criteria identified. As stated above, some embodiments may have criteria that requires certain outcome values to exceed a threshold. The requirement can be the outcome value is below or above the threshold. Multiple thresholds for different outcome values can be specified. Further, different combinations of thresholds can be specified for different outcome values. For example, when the first outcome value can be required to be above the first threshold. However, if the first outcome is value below first threshold, but above and intermediate threshold, the treatment plan may satisfy the constraints if a second outcome value is above the second threshold.

In step 740, one or more quality scores are assigned to each treatment plan using remaining criteria. As an example, the remaining criteria can be a formula for calculating a quality score. Multiple quality scores can be determined, each using different criteria. Examples of formulas include a weighted average of the quality scores, where different quality scores can use different weights. The treatment plans can be displayed or otherwise output with one or more quality scores provided a location corresponding to a respective treatment plan.

In step 750, treatment plans can be sorted by a designated quality score. For example, a user may specify that a particular quality score (which may be equal to a particular outcome value) is of prime importance, and thus the treatment plans are to be sorted based on that designated quality score. For example, a doctor may want to identify treatment plan with the smallest treatment time.

Quality scores can summarize the overall quality for treatment for a specific case. For example, if a parotid for a specific patient is already damaged or removed, additional radiation damage to it is not that important. Also, there could be other patient specific considerations. The patient could have another medical condition that makes some side effects very difficult to live with. As another example, the patient could have a profession that makes hearing with both ears or seeing with both eyes important.

VII. Computer System

Any of the computer systems mentioned herein may utilize any suitable number of subsystems. Examples of such subsystems are shown in FIG. 8 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 8 are interconnected via a system bus 875. Additional subsystems such as a printer 874, keyboard 878, storage device(s) 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 (e.g. Ethernet, Wi-Fi, etc.) can be used to connect computer system 800 to a wide area network such as the Internet, a mouse input device, or a scanner. The interconnection via system bus 875 allows the central processor 873 to communicate with each subsystem and to control the execution of instructions from system memory 872 or the storage device(s) 879 (e.g., a fixed disk, such as a hard drive or optical disk), as well as the exchange of information between subsystems. The system memory 872 and/or the storage device(s) 879 may embody a computer readable medium. Any of the data mentioned herein can be output from one component to another component and can be output to the user.

A computer system can include a plurality of the same components or subsystems, e.g., connected together by external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of selecting among a plurality of treatment plan types for treating a tumor of a first patient, the method comprising:

for each of the plurality of treatment plan types:
creating, by a computer system, an estimation function associated with the treatment plan type by:
receiving previous outcome values of one or more types of outcome values for previous patients treated using the treatment plan type,
receiving previous input values of input variables for the previous patients, for each of the one or more types of outcome values:
using the previous input values and the previous outcome values corresponding to the type of outcome value to determine an estimation sub-function of the estimation function;

receiving, by the computer system, information about the first patient;

analyzing, by the computer system, the information to determine a set of input values, the input values including characteristics of the tumor;

for each of the plurality of treatment plan types:
identifying an estimation function associated with the treatment plan type, and
predicting a quality of the treatment plan type by using the set of input values with the identified estimation function to calculate, by the computer system, one or more outcome values, and determining a quality score based on the one or more outcome values, the set of input values including the one or more dose input values;

identifying, by the computer system, a first treatment plan type having an optimal quality score to a user of the computer system, the first treatment plan type including providing radiation to the first patient;

generating, by the computer system, a first treatment plan of the first treatment plan type based on the set of input values and the plurality of outcome values, the first treatment plan including instructions for controlling a treatment head in order to treat the tumor of the first patient; and providing, by the treatment head coupled with a radiation source, radiation at pre-defined angles and pre-defined doses to specific portions of a treatment area of the first patient according to the first treatment plan, wherein the treatment head is controlled by a control unit according to the instructions in the first treatment plan.

2. The method of claim 1, further comprising:
comparing, by the computer system, the quality scores of the treatment types to identify the first treatment plan type having the optimal quality score.

3. The method of claim 1, wherein calculating a first outcome value includes:
predicting a dose distribution based on the set of input values; and
using the predicted dose distribution to determine the first outcome value.

4. The method of claim 1, wherein using the previous input values and the previous outcome values corresponding to the type of outcome value to determine an estimation subfunction of the estimation function includes:
plotting data points of the previous input values and the previous outcome values corresponding to the type of outcome value; and
using a distance between the data points to compute a mapping function from the input variables to the previous outcome values, wherein the mapping function corresponds to the estimation subfunction of the estimation function.

5. The method of claim 1, wherein identifying the first treatment plan type includes:
outputting the treatment plan types with the corresponding quality scores.

6. The method of claim 1, wherein the treatment plan types include chemotherapy and surgery.

7. The method of claim 1, wherein a plurality of outcome values are calculated from each of at least one of the respective estimation functions corresponding to at least one of the treatment plan types, the method further comprising:
for each of the at least one of the treatment plan types:
using a quality function to determine the quality score from the plurality of outcome values, wherein each outcome value is determined by a respective estimation subfunction.

8. The method of claim 7, further comprising:
determining the quality function based on criteria provided by the user of the computer system.

9. The method of claim 1, wherein the quality score is one of the outcome values.

10. The method of claim 9, wherein identifying the first treatment plan type includes:
sorting the quality scores in response to criteria from the user.

11. A computer product comprising a non-transitory computer readable medium storing a plurality of instructions that when executed control a computer system to select among a plurality of treatment plan types for treating a tumor of a first patient, the instructions comprising:
receiving information about the first patient;
analyzing the information to determine a set of input values, the input values including characteristics of the tumor;
selecting, from a plurality of dose prediction models, a dose prediction model corresponding to a particular treatment plan type;
using the dose prediction model to predict a dose distribution of radiation to be provided to the tumor for the particular treatment plan based on the characteristics of the tumor, the dose distribution specifying a variation of radiation dose within the tumor;
determining one or more dose input values from the predicted dose distribution for the particular treatment plan type;
for each of the plurality of treatment plan types:
identifying an estimation function associated with the treatment plan type, the estimation function generated based on outcomes of other patients using the treatment plan type, and
predicting a quality of the treatment plan type by using the set of input values with the identified estimation function to calculate one or more outcome values, the set of input values including the one or more dose input values for the particular treatment plan type, and by determining a quality score based on the one or more outcome values, the set of input values including the one or more dose input values; and
identifying a first treatment plan type having an optimal quality score to a user of the computer system, the first treatment plan type including providing radiation to the first patient;
generating a first treatment plan of the first treatment plan type based on the set of input values and the plurality of outcome values, the first treatment plan including instructions for controlling a treatment head in order to treat the tumor of the first patient; and
providing, by the treatment head coupled with a radiation source, radiation at pre-defined angles and pre-defined doses to specific portions of a treatment area of the first patient according to the first treatment plan, wherein the treatment head is controlled by a control unit according to the instructions in the first treatment plan.

12. The method of claim 4, wherein the estimation function for each treatment plan type includes a plurality of estimation subfunctions, wherein each of the one or more outcome values are determined by a respective estimation subfunction, wherein each estimation subfunction corresponds to a multidimensional surface, and wherein each input variable corresponds to a different dimension in the multidimensional surface plot.

13. The method of claim 1, wherein each outcome value corresponds to either a biological effect on the patient or a property of the treatment.

14. The method of claim 13, wherein the outcome values include at least one of a probability of treatment success, a quality of life indicator, a probability of organ failure, a treatment time, and a recovery time.

15. The method of claim 1, wherein analyzing the information to determine a set of input values includes:
identifying specific values within the first patient information that correspond to input variables for the first estimation function,
wherein the input variables are included in the estimation function because they correlate with the outcome values more strongly than other types of the patient information.

16. A radiation therapy system comprising:
a radiation therapy device including:
a rotatable gantry including a treatment head and a multileaf collimator, wherein the multileaf collimator is configured to shape a radiation beam emitted from the treatment head; and
a control unit configured to:

control the rotation of the rotatable gantry,
control emission of the radiation beam from the treatment head, and
control the shape of the radiation beam via the multileaf collimator;
wherein the radiation therapy device is configured to:
receive a first treatment plan of a first treatment plan type; and
provide the radiation beam at pre-defined angles and pre-defined doses to specific portions of a treatment area of a first patient according to instructions in the first treatment plan;
one or more processors; and
a non-transitory computer readable medium for controlling the one or more processors, the computer readable medium storing a plurality of instructions that when executed control the one or more processors to select among a plurality of treatment plan types for treating a tumor of the first patient, the instructions comprising:
receiving information about the first patient;
analyzing the information to determine a set of input values, the input values including characteristics of the tumor;
predicting, using a dose prediction model, a dose distribution of radiation to be provided to the tumor based on the characteristics of the tumor, the dose distribution specifying a variation of radiation dose within the tumor;
determining one or more dose input values from the predicted dose distribution;
for each of the plurality of treatment plan types:
identifying an estimation function associated with the treatment plan type, the estimation function generated based on outcomes of other patients using the treatment plan type, and
predicting a quality of the treatment plan type by using the set of input values with the identified estimation function to calculate, by the computer system, a plurality of outcome values and determining a quality score based on the plurality of outcome values, the set of input values including the one or more dose input values;
identifying the first treatment plan type having an optimal quality score, the first treatment plan type including providing radiation to the first patient;
generating the first treatment plan of the first treatment plan type based on the set of input values and the plurality of outcome values, the first treatment plan including instructions for controlling the rotation of the rotatable gantry, the emission of the radiation beam from the treatment head, and the shape of the radiation beam via the multileaf collimator in order to treat the tumor of the first patient according to the predicted dose distribution; and
providing the first treatment plan from the one or more processors to the control unit of the radiation therapy device.

17. The method of claim 4, wherein computing at least one of the mapping functions includes clustering of the data points or performing a functional fit of the data points.

18. The method of claim 1, wherein providing radiation to specific portions of a treatment area of the first patient causes shrinking of a tumor in the treatment area.

* * * * *